United States Patent
Nagata et al.

(10) Patent No.: US 7,290,879 B2
(45) Date of Patent: Nov. 6, 2007

(54) EYE REFRACTIVE POWER MEASUREMENT DEVICE

(75) Inventors: Tatsuhiko Nagata, Tokyo (JP); Eishi Aizawa, Tokyo (JP); Tetsurou Nishida, Tokyo (JP)

(73) Assignee: Right Mfg. Co., Ltd., Tokyo (JP)

( * ) Notice: Subject to any disclaimer, the term of this patent is extended or adjusted under 35 U.S.C. 154(b) by 124 days.

(21) Appl. No.: 11/320,983

(22) Filed: Dec. 30, 2005

(65) Prior Publication Data

US 2007/0008490 A1    Jan. 11, 2007

(51) Int. Cl.
*A61B 3/10* (2006.01)

(52) U.S. Cl. .................................. 351/205

(58) Field of Classification Search ............... 359/205
See application file for complete search history.

(56) References Cited

U.S. PATENT DOCUMENTS

| | | | |
|---|---|---|---|
| 4,353,625 A | 10/1982 | Nohda et al. | |
| 5,428,414 A | 6/1995 | Iwane | |
| 5,555,039 A | 9/1996 | Iki et al. | |
| 5,872,614 A * | 2/1999 | Ueno | 351/211 |

OTHER PUBLICATIONS

Kajita Masaoshi et al., "Eye Accomodation Function Measurement Unit", Japanese Patent Publication No. 2003-070740, Publication Date: Mar. 11, 2003.

* cited by examiner

*Primary Examiner*—Ricky Mack
*Assistant Examiner*—William C Choi

(57) ABSTRACT

The present invention provides a compound device having an eye refractive power measurement function and an eye accommodation function state measurement function, preventing an increase in size and cost in comparison with a known eye refractive power measurement device, and convenient for the operator even when the measurement type is changed. An eye refractive power measurement device includes a measurement type select switch (30) which selects one of at least two types of measurements including normal refractive power measurement, which measures the refractive power of the subject s eye including spherical power, cylinder power, and astigmatism axis, and eye accommodation function state measurement, which determines a change in the refractive power of the subject s eye for high-frequency components. A refractive power measurement section (40) is a multiple meridian direction refractive power measurement section which can measure the eye refractive power in two or more meridian directions. The multiple meridian direction refractive power measurement section measures the refractive power in at least two meridian directions when performing the normal refractive power measurement. The multiple meridian direction refractive power measurement section measures the refractive power in one predetermined meridian direction when performing the eye accommodation function state measurement.

5 Claims, 6 Drawing Sheets

EYE REFRACTIVE POWER MEASUREMENT DEVICE

TECHNICAL FIELD

The present invention relates to an eye refractive power measurement device which measures the refractive power and the accommodation function state of the subject s eye.

BACKGROUND ART

In the field of medical treatment such as ophthalmology, a refractive power measurement device which measures the eye refractive power has been widely used. An example of the refractive power measurement device is a refractive power measurement device using retinoscopy such as the types disclosed in patent documents 1 and 2. In the field of medical treatment including ophthalmology, measurement of the eye accommodation function state has also been demanded as a more detailed refraction state. For example, a device which objectively measures the eye accommodation function state has been proposed, such as an eye accommodation function state measurement device disclosed in patent document 3.

In eye accommodation function state measurement, the eye refractive power is continuously measured at high speed by utilizing a known refractive power measurement method (e.g. method disclosed in the patent document 2). Therefore, since an eye accommodation function state measurement device is generally similar to a known eve refractive power measurement device, a compound device enabling normal eye refractive power measurement (hereinafter may be called normal measurement) and eye accommodation function state measurement increases efficiency and convenience.

(Patent document 1) JP-A-55-160538
(Patent document 2) JP-A-6-165757
(Patent document 3) JP-A-2003-70740

According to the patent document 3, an eye accommodation function state measurement device must continuously measure the refractive power at a frequency of 1 Hz to 2.3 Hz. An eye refractive power measurement section can obtain measurement values at measurement intervals of 0.1 second when the frequency is set at 1 Hz, and can obtain measurement values at measurement intervals of 0.05 seconds when the frequency is set at 2 Hz. And in the meantime the high-frequency components cannot to be obtained unless the measurements are continuously performed. However, a known eye refractive power measurement device requires a measurement time of at least about 0.2 seconds per measurement. Therefore, since it is difficult to directly apply a known eye refractive power measurement device to an eye accommodation function state measurement device, an eye refractive power measurement device must be improved or modified so that continuous measurement can be performed at higher speed.

For example, when using the refractive power measurement method disclosed in the patent document 1, an optical system including a prism is caused to make a round by a motor in parallel to the meridian direction in order to measure the eye refractive power in all meridian directions. In order to measure the refractive power within 0.1 second or less per measurement, the optical system must be rotated at a higher speed than in a known device. Therefore, the size of the motor must be increased in order to increase the rotational speed of the motor, the rigidity of the device must be increased in order to allow continuous rotation, or a high-speed processing circuit is required in order to perform high-speed measurement processing. This results in an increase in size and cost in comparison with a known device.

A compound device may suffer from a display difficulty if the normal refractive power measurement is performed at high speed in the same manner as the eye accommodation function state measurement device. Therefore, operability (convenience) may be decreased due to an increase in speed.

DISCLOSURE OF THE INVENTION

An objective of the present invention is to provide a compound device having an eye refractive power measurement function and an eye accommodation function state measurement function, preventing an increase in size and cost in comparison with a known eye refractive power measurement device, and convenient for the operator even when the measurement type is changed.

The present invention achieves the above objective by providing the following solution means. The solution means is described below using symbols corresponding to symbols used in embodiments of the present invention so that the solution means is readily understood. However, the solution means is not limited thereto.

A first invention provides an eye refractive power measurement device comprising: a refractive power measurement section (40, 61) which measures refractive power of a subject s eye; a measurement type select section (30, 68) which selects one of at least two types of measurements including normal refractive power measurement, which measures the refractive power of the subject s eye including spherical power, cylinder power, and astigmatism axis, and eye accommodation function state measurement, which determines a change in the refractive power of the subject s eye for high-frequency components; and a control section (20, 65) which changes a measurement operation corresponding to the measurement type selected by the measurement type select section.

A second invention provides the eye refractive power measurement device according to the first invention, wherein the measurement operation is changed by changing a number of measurement meridian directions (S2, S5).

A third invention provides the eye refractive power measurement device according to the first invention, wherein the measurement operation is changed by changing a number of measurement samplings for obtaining one measured value (S12, S17).

A fourth invention provides the eye refractive power measurement device according to the first invention, wherein the measurement operation is changed by changing a measurement interval from one measurement to next measurement.

A fifth invention provides the eye refractive power measurement device according to the first invention, comprising: a motor (61i) for projecting a measurement striped pattern onto the subject s eye and moving the striped pattern relative to the subject s eye; wherein the measurement operation is changed by changing a rotational speed of the motor.

A sixth invention provides the eye refractive power measurement device according to the first or second invention, wherein the refractive power measurement section includes a multiple meridian direction refractive power measurement section (40) which can measure the refractive power in two or more meridian directions; wherein, when performing the normal refractive power measurement, the multiple meridian direction refractive power measurement section measures the refractive power in at least two meridian directions (S2); and wherein, when performing the eye accommodation function state measurement, the multiple meridian direction refractive power measurement section measures the refractive power in one predetermined meridian direction (S5).

A seventh invention provides the eye refractive power measurement device according to any of the first to sixth inventions, comprising: a high-frequency component input section (69) which allows selection or input of a high-frequency component value within a range of 1 Hz to 2.3 Hz; wherein the control section (65) changes the measurement operation of the refractive power measurement section corresponding to the high-frequency component value input from the high-frequency component input section.

According to the present invention, a compound device having an eye refractive power measurement function and an eye accommodation function state measurement function can be provided which prevents an increase in size and cost in comparison with a known eye refractive power measurement device and is convenient for the operator even when the measurement type is changed.

BRIEF DESCRIPTION OF THE DRAWINGS

FIG. 5 is a diagram showing a striped pattern of a chopper 61a.

BEST MODE FOR CARRYING OUT THE INVENTION

Preferred embodiments of the present invention are described below in detail with reference to the drawings.

First Embodiment

Figure 1:
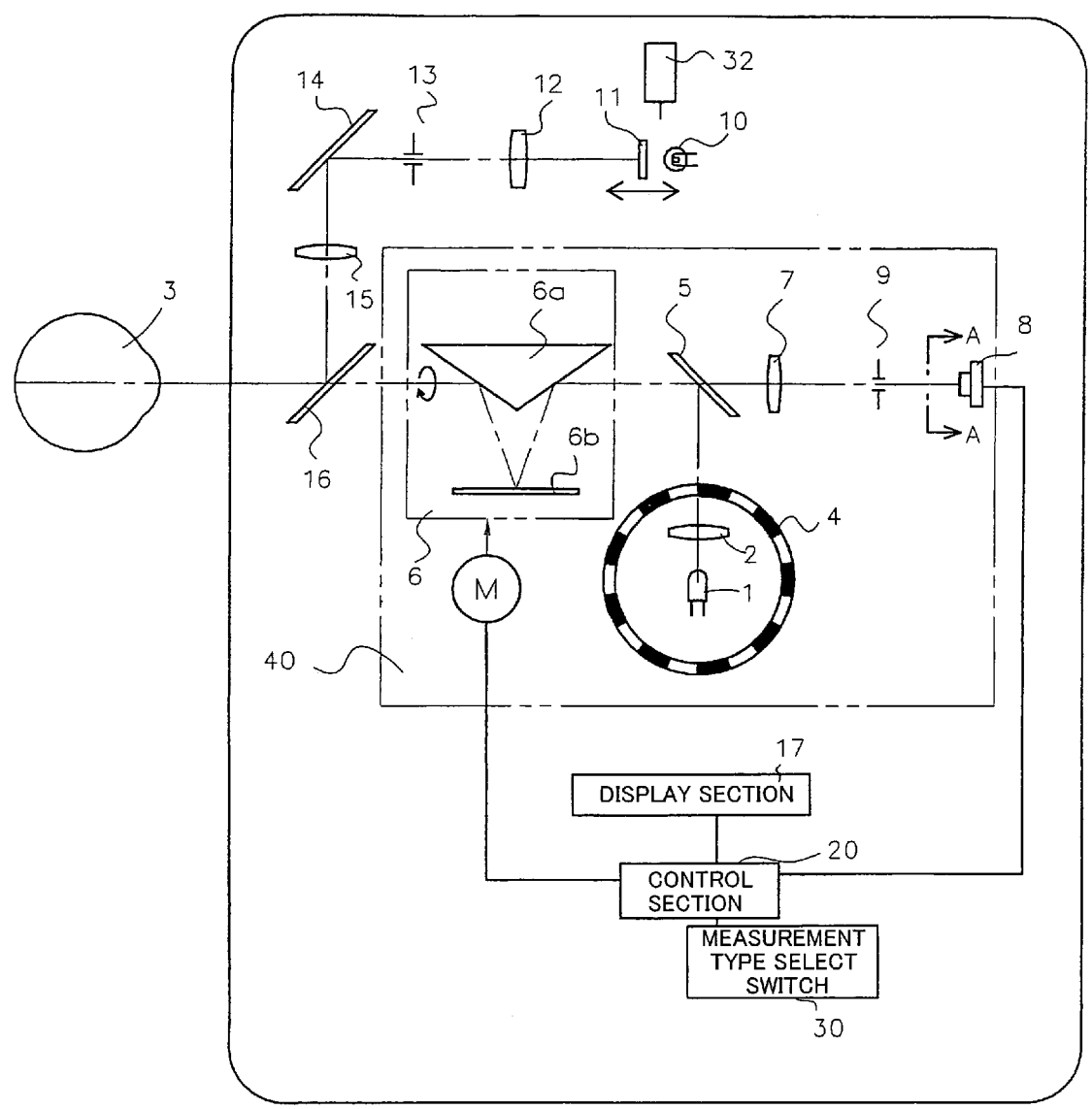
FIG. 1 is a diagram showing a configuration of an optical system of an eye refractive power measurement device according to a first embodiment of the present invention.

FIG. 1 is a diagram showing a configuration of an optical system of an eye refractive power measurement device according to a first embodiment of the present invention.

Figure 2:
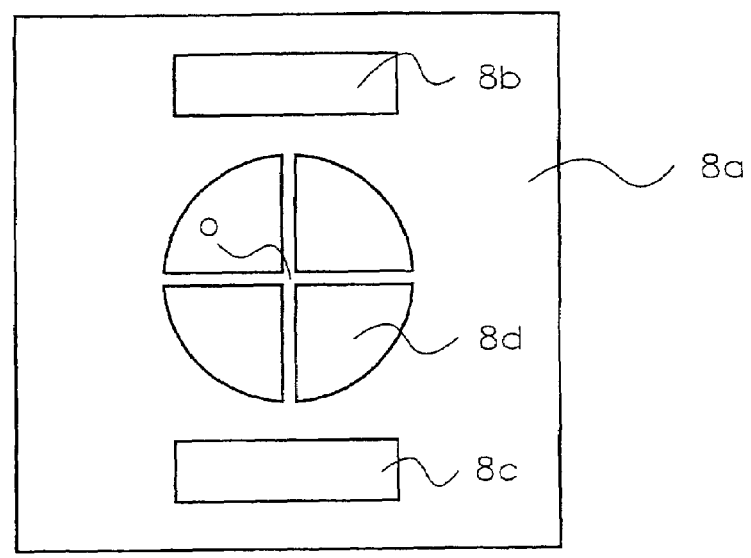
FIG. 2 is a diagram showing a photoelectric conversion element 8 used in the first embodiment viewed along the line A-A shown in FIG. 1.

FIG. 2 is a diagram showing a photoelectric conversion element 8 used in the first embodiment viewed along the line A-A shown in FIG. 1.

The eye refractive power measurement device according to the first embodiment includes a refractive power measurement section 40 and a fogging device. The measurement principle of the refractive power measurement section 40 is retinoscopy, in which the eye refractive power is measured by detecting the moving speed of a shadow on the pupil. An objective eye refractive power measurement device using retinoscopy is disclosed in JP-A-55-86437, for example. The configuration of the device used in the present invention is basically the same as that of the device disclosed in JP-A-55-86437. Therefore, description of the details of the measurement principle is omitted.

As shown in FIG. 1, the optical system of the refractive power measurement section 40 includes a light emitting diode 1, a condenser lens 2, a chopper 4, a half mirror 5, a measurement diameter rotation system 6, an objective lens 7, a light receiving section 8, and a diaphragm 9. The optical system of the fogging device 15 includes a visible light source 10, a fixation target 11, a holding member 32, a projection lens 12, a diaphragm 13, a mirror 14, a lens 15, and a dichroic mirror 16. The eye refractive power measurement device also includes a control section 20, a measurement type select section 30, and a display section 17.

An image formed by infrared light emitted from the light emitting diode 1 is converged (imaged) on the pupil of a subject s eye 3 by the condenser lens 2. The light emitting diode 1 and the condenser lens 2 are surrounded by the chopper 4 formed by a hollow cylinder. A plurality of slits are formed in the chopper 4 along the circumference of the chopper 4. The longitudinal direction of the slit is perpendicular to the plane of FIG. 1.

The chopper 4 can be rotated around the light emitting diode 1 by a drive system not shown in FIG. 1. A linear luminous flux which has passed through the slit formed in the chopper 4 is incident on the half mirror 5. The half mirror 5 reflects infrared light from the light emitting diode 1 toward the subject s eye 3, and transmits light reflected by the subject s eye 3.

The device shown in FIG. 1 further includes the measurement diameter rotation system 6 including a prism 6a and a mirror 6b. The measurement diameter rotation system 6 is used to observe the astigmatism state of the subject s eye 3. The meridian direction of the linear luminous flux incident on the subject s eye 3 is sequentially changed by rotating the measurement diameter rotation system 6 stepwise around an optical axis A. Specifically, the measurement diameter rotation system 6 enables measurement in two or more meridian directions. Light reflected by the subject s eye 3 passes through the measurement diameter rotation system 6 and the half mirror 5 and is incident on the objective lens 7. The image on the pupil of the subject s eye 3 passes through the objective lens 7 and is converged (imaged) on the light receiving section 8 through the diaphragm 9. The diaphragm 9 has a rectangular opening of which the longitudinal direction is perpendicular to the plane of FIG. 1. The opening is approximately positioned at the focus of the objective lens 7.

As shown in FIG. 2 (cross section along the line A-A shown in FIG. 1), the light receiving section 8 includes a substrate 8a, refractive power measurement photoelectric conversion elements 8b and 8c secured on the substrate 8a, and displacement detection quadrant photoelectric conversion element 8d. As shown in FIG. 2, the photoelectric conversion elements 8b and 8c are disposed in the scan direction of the linear luminous flux on the subject s eye 3. The quadrant photoelectric conversion element 8d disposed between the photoelectric conversion elements 8b and 8c is formed by four photoelectric conversion elements to detect the optical center. A center O of the four photoelectric conversion elements coincides with the optical axis A of the objective lens 7.

The fixation target 11 and the visible light source 10 are reciprocated in the optical axis direction by the operation of the motor 32. An image of the fixation target 11 illuminated by the visible light source 10 is reflected by the mirror 14 after passing through the projection lens 12 and the diaphragm 13, and is incident on the lens 15. The image of the fixation target 11 which has passed through the lens 15 is reflected by the dichroic mirror 16 toward the subject s eye 3, and is projected onto the retina through the lens of the subject s eye 3.

The refractive power is detected by measuring the phase difference between signals output from the photoelectric conversion elements 8b and 8c. Specifically, since the fundus of the subject s eye 3 is scanned by the linear luminous flux due to rotation of the chopper 4, the position of the slit 9 corresponds to the neutral point when the subject s eye 3 is emmetropic. Therefore, since the luminous flux emitted through the slit 9 becomes uniformly brighter and darker, the signals output from the photoelectric conversion elements 8b and 8c have an identical phase.

When the subject s eye 3 is not emmetropic, light and shade stripes corresponding to the refractive error state of the eye are emitted through the slit 9. Therefore, the signals output from the photoelectric conversion elements 8b and 8c differ in phase depending on the refractive error state of the subject s eye. Therefore, the refractive power of the subject s eye can be determined from the phase difference between the signals output from the photoelectric conversion elements 8b and 8c.

The refractive power of the subject s eye can be determined from the phase difference between the signals output from the photoelectric conversion elements 8b and 8c only in one meridian direction. In order to measure the refractive power of the entire eye, the refractive power is measured in all meridian directions by rotating the measurement diameter rotation system 6 stepwise. Data generally employed as the refractive power, such as the maximum refractive power, minimum refractive power, meridian lines respectively corresponding to the maximum and minimum refractive powers, spherical power (S), cylinder power (C), and astigmatism axis (AX), is calculated by the control section 20 from the measured values.

The details regarding the method by which the control section 20 changes the measurement operation using the device having the above-described configuration when normal measurement or eye accommodation function state measurement is selected is described below with reference to FIG. 3.

Figure 3:
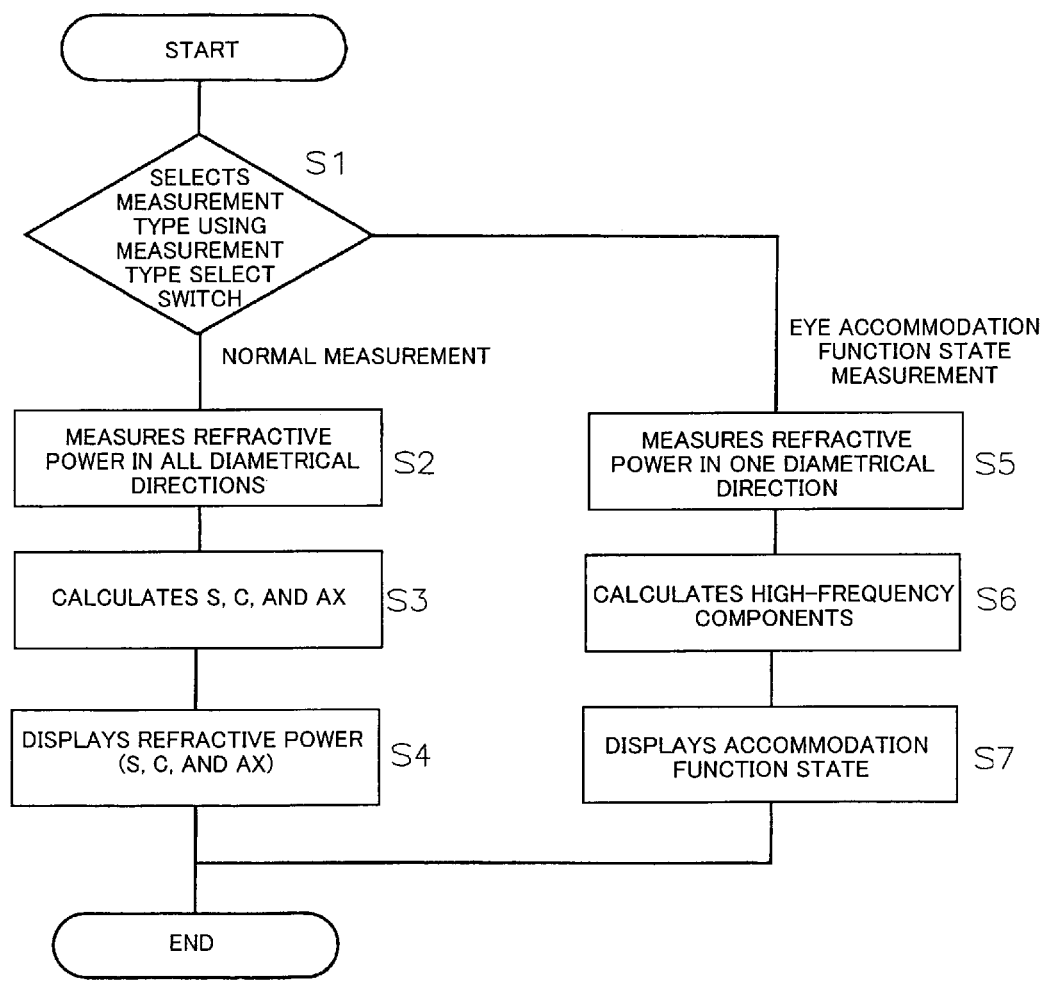
FIG. 3 is a flowchart of the operation of a control section 20.

FIG. 3 is a flowchart of the operation of the control section 20.

The operator selects the measurement type using the measurement type select switch (measurement type select section) 30 (step S1). The control section 20 selects the measurement time corresponding to the selected measurement type (normal measurement or eye accommodation function state measurement) (step S2 or S5). The operation is described below for each measurement type.

(When Normal Measurement is Selected)

The refractive power is measured in all meridian directions by rotating the measurement diameter rotation system 6 stepwise as described above (step S2). Data generally employed as the refractive power, such as the maximum refractive power, minimum refractive power, meridian lines respectively corresponding to the maximum and minimum refractive powers, spherical power (S), cylinder power (C), and astigmatism axis (AX), is calculated by the control section 20 from the measured values (step S3). The refractive power (e.g. spherical power (S), cylinder power (C), and astigmatism axis (AX)) calculated from the measured values is displayed in the display section 16 to indicate the measurement results to the operator (step S4). The measurement is thus completed.

(When Eye Accommodation Function State Measurement is Selected)

The refractive power is measured without rotating the measurement diameter rotation system 6 (step S5). Since the eye accommodation function state measurement aims at observing a sequential change in the refractive power, the aim can be achieved without measuring the refractive power in all meridian directions. The refractive power may also be measured in all meridian directions. However, since the measurement diameter rotation system 6 is large and heavy due to inclusion of the prism 6a, it is difficult to continuously measure the refractive power at measurement intervals of 0.1 second or less while rotating the measurement diameter rotation system 6. The control section 20 chooses the fastest measurement operation for obtaining necessary information. After calculating high-frequency components from the measured values (step S6), the accommodation function state is displayed in the display section 16 to indicate the measurement results to the operator (step S7). The measurement is thus completed. In the actual measurement, the refractive power is repeatedly measured while moving the target. The details of the measurement method, calculation of high-frequency components, and the details of the accommodation function state display method are basically the same as those of the eye accommodation function state measurement device disclosed in the patent document 3. Therefore, description of these items is omitted.

When measuring the refractive power without rotating the meridian direction (step S5), the meridian direction may be an arbitrary direction. In the first embodiment, the measurement diameter rotation system 6 is fixed in one direction when the eye accommodation function state measurement is selected. Note that the measurement diameter rotation system 6 may be rotated by reduced rotational steps in comparison with the normal measurement insofar as the measurement time can be set at 0.1 second or less.

Second Embodiment

A second embodiment of the present invention is described below with reference to FIGS. 4, 5, and 6.

Figure 4:
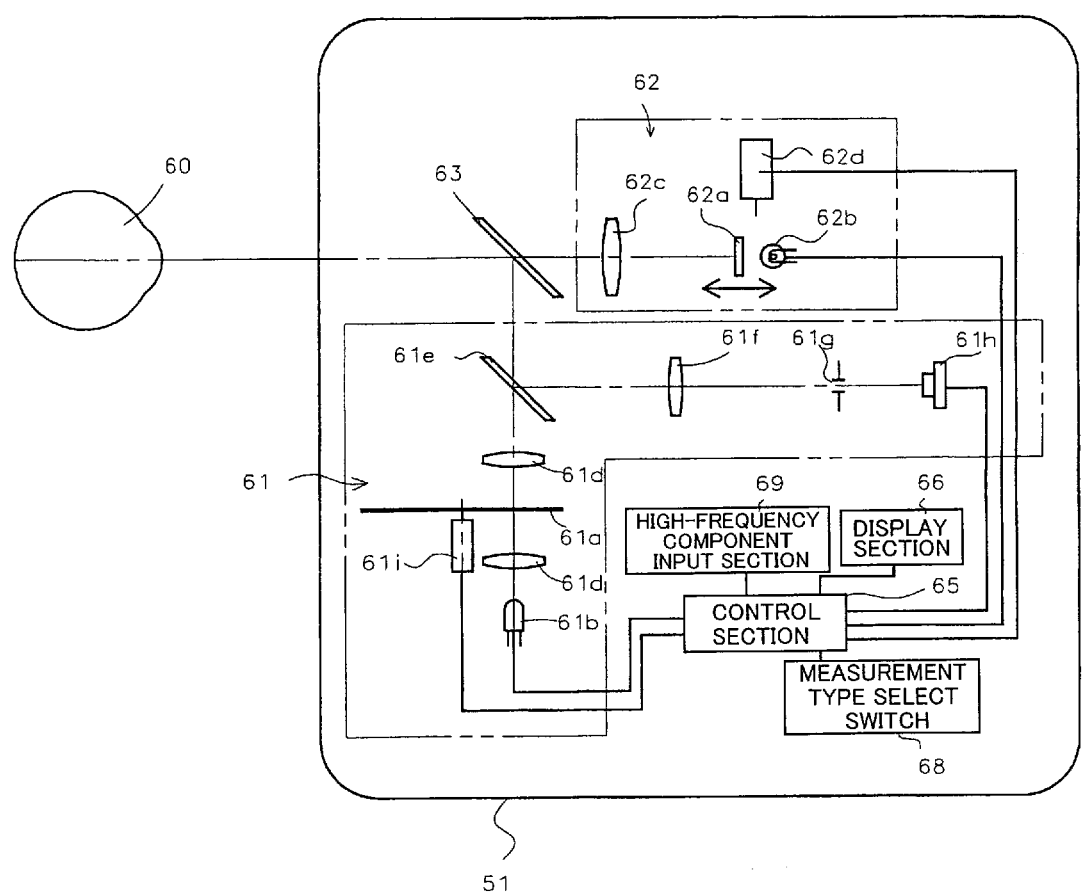
FIG. 4 is a configuration diagram of an eye refractive power measurement device 51 according to a second embodiment.

FIG. 4 is a configuration diagram of an eye refractive power measurement device 51 according to the second embodiment.

The configuration of the device used in the present invention is the same as that of the devices disclosed in the patent documents 1 and 2. The device according to the second embodiment uses retinoscopy similar to that used in the first embodiment. The basic principle for obtaining one refraction measurement is similar to that disclosed in the patent documents 1 and 2. Therefore, the details of the measurement principle are omitted. As shown in FIG. 4, the eye refractive power measurement device 51 includes a refraction measurement section 61, a projection section 62, a dichroic mirror 63, a control section 65, a display section 66, a measurement type select section 68, a high-frequency component input section 69, and the like. The projection section 62 includes a target 62a, a light source (visible light source) 62b, a convex lens 62c, and a motor 62d. The target 62a and the light source (visible light source) 62b can be moved in the optical axis direction (direction indicated by the arrows in FIG. 4) by a target moving mechanism (not shown) by means of rotation of the motor 62d.

In the projection section 62, the convex lens 62c, the target 62a, and the light source 62b are disposed from the side near a subject s eye 60. A luminous flux from the target 62a illuminated by the light source 62b is incident on the subject s eye 60 after being converted into a state close to a parallel luminous flux by the convex lens 62c. Therefore, the target 62a is seen at a position farther than the actual position.

The target 62a and the light source 62b can be moved by the target moving mechanism 62d and the motor 62e in the direction of the optical axis of the subject s eye 60 while maintaining a constant positional relationship between the target 62a and the light source 62b.

The refraction measurement section 61 includes the chopper 61a having slits formed therein, a motor 61i which rotates the chopper 61a, a light source (infrared light source) 61b which illuminates the chopper 61a, a lens 61d which projects a striped pattern formed by the chopper 61a onto the fundus of the subject s eye 60, a light receiving section 61h which detects the moving velocity of the striped pattern formed by light returned from the fundus of the subject s eye 60, optical systems 61f and 61g, and the like (61f and 61c indicate lenses, 61e indicates a half mirror, and 61g indicates a diaphragm).

The dichroic mirror 63 respectively guides measurement light (infrared light) emitted from the refraction measurement section 61 and measurement light (visible light) emitted from the projection section 62 to the subject s eye 60, and returns the infrared light from the subject s eye 60 to the refraction measurement section 61. In the refraction measurement section 61, the chopper 61a rotates so that the striped pattern projected onto the fundus of the subject s eye 60 moves. The moving velocity of the striped pattern formed on the light receiving section 61h changes corresponding to the refractive power of the subject s eye 60.

Figure 5:
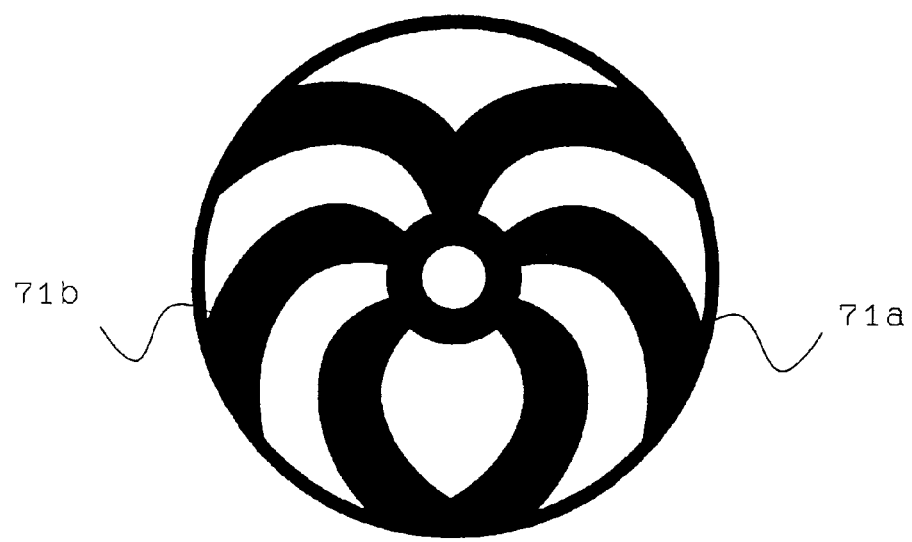

FIG. 5 is a diagram showing the striped pattern of the chopper 61a.

As shown in FIG. 5, stripes 71a and 71b in two directions are formed on the chopper as the striped pattern of the chopper 61a. When the chopper 61a has made a round, the measurement is performed in two meridian directions so that the refractive power such as the spherical power, the cylinder power, and the astigmatic axis are calculated.

In the second embodiment, one measurement value (sampling value described later) can be obtained by one round of the motor 61i (one round of the chopper 61a).

The control section 65 includes a CPU, a circuit including a memory used for the operation of the CPU, and the like. The control section 65 controls the operations of the light sources 62b and 61b, the motors 62e and 61i, and the display section 66, and performs calculations by referring to signals output from the light receiving section 61h. In more detail, the control section 65 disposes the target 62a (target 62a and light source 62b) and scans the position of the target 62a by referring to the output from the refraction measurement section 61 while driving the refraction measurement section 61 (controlling the operation of the motor 62e while driving the light source 62b).

The control section 65 measures the refractive power of the subject s eye 60 by referring to the output from the light receiving section 61h while driving the light source 61b, the motor 61i, and the light receiving section 61h.

The details regarding the method by which the control section 65 changes the measurement time using the device having the above-described configuration when the normal refractive power measurement or the eye accommodation function state measurement is selected are described below with reference to FIG. 6.

Figure 6:
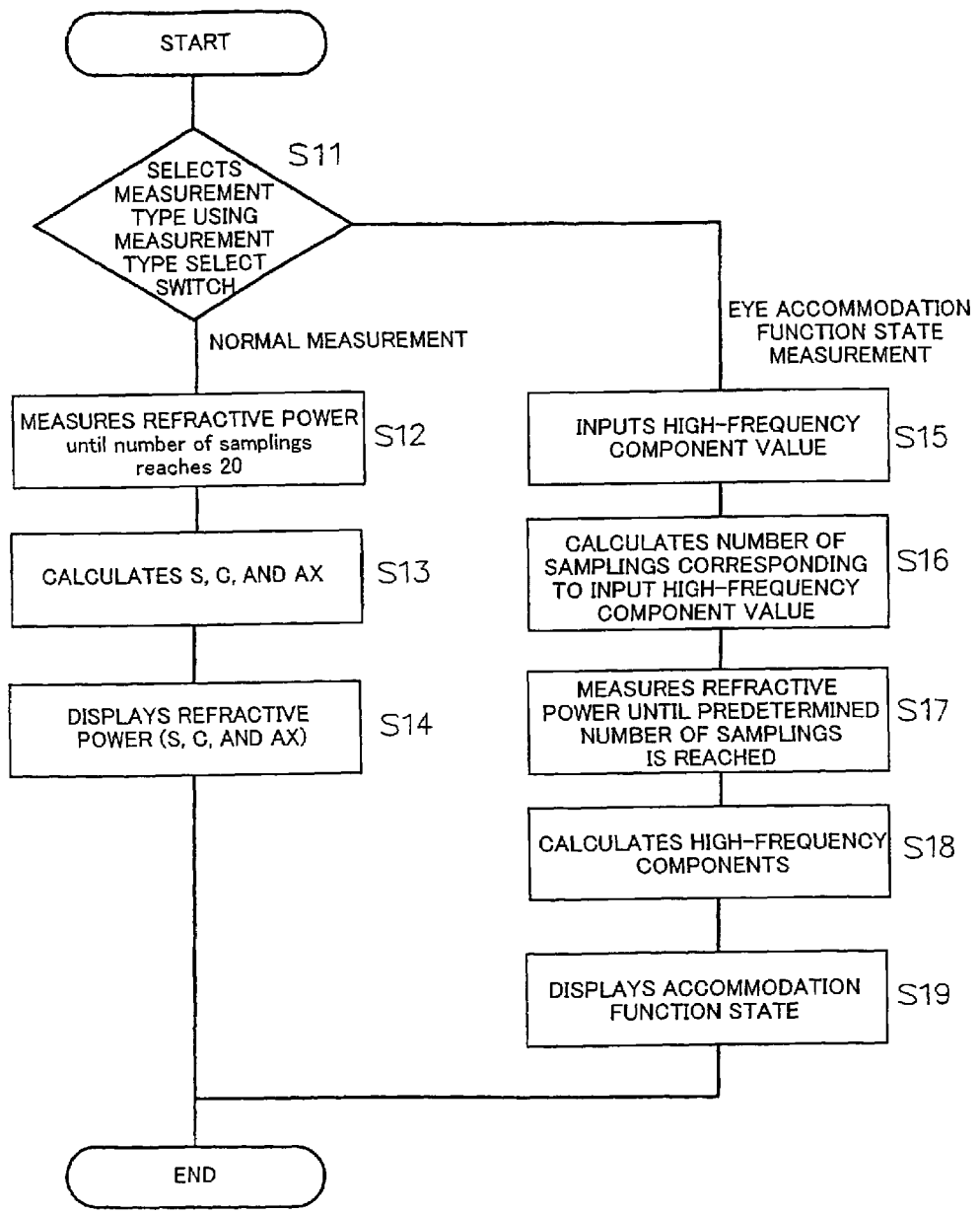
FIG. 6 is a flowchart of the operation performed by a control section 65.

FIG. 6 is a flowchart of the operation of the control section 65.

The operator selects the measurement type using the measurement type select section 68 (step S11). The control section 15 selects the measurement time corresponding to the selected measurement type (step S12 or S15). The operation is described below for each measurement type.

(When Normal Measurement is Selected)

In the second embodiment, the measurement value (sampling value) can be obtained by one round of the motor 61i (one round of the chopper 61a). In the second embodiment, the measurement operation by one round is defined as one sampling, and sampling is performed 20 times in order to obtain the final measurement value (step S11). For example, when the motor 61i rotates at 6000 rpm, 0.01 second is required to make a round. However, since inconvenience such as a display difficulty occurs when the measurement interval is as short as 0.01 second, the number of samplings is increased so that the optimum measurement interval (0.2 seconds) is achieved. The number of samplings may be set at one, and the measurement may be conducted at intervals of 0.2 seconds. In the second embodiment, the maximum number of samplings is selected within the measurement interval in order to ensure measurement stability taking occurrence of a blink or eye movement into consideration.

The refractive power such as the maximum refractive power, minimum refractive power, meridian lines respectively corresponding to the maximum and minimum refractive powers, spherical power (S), cylinder power (C), and astigmatism axis (AX) is calculated by the control section 20 from the measured values (step S13). Since the number of samplings is 20, the refractive power may be determined by averaging the measured values, or the intermediate measured value may be selected as the refractive power. The refractive power (e.g. spherical power S, cylinder power C, and astigmatism axis AX) calculated from the measured values is displayed in the display section 66 to indicate the measurement results to the operator (step S14). The measurement is thus completed.

(When Eye Accommodation Function State Measurement is Selected)

According to the patent document 3, the eye accommodation function state measurement device requires continuous refractive power measurement at a frequency of 1 Hz to 2.3 Hz. The eye refractive power measurement section measures the refractive power at intervals of 0.1 second when the frequency is set at 1 Hz, and measures the refractive power at intervals of 0.05 second when the frequency is set at 2 Hz. Specifically, the eye refractive power measurement section must obtain the measurement values at intervals of 0.1 second or less. The operator selects a desired measurement target high-frequency component within the range of 1 Hz to 2.3 Hz using the high-frequency component input section 69 (step S15). The high-frequency component input section 69 may be a value input key pad such as a ten-key pad, or may allow selection from values provided in advance. The control section 65 determines the eye accommodation function state measurement time corresponding to the high-frequency component value selected using the high-frequency component input section 69. For example, the control section 65 sets the measurement time at 0.1 second when 1 Hz is selected, and sets the measurement time at 0.05 second when 2 Hz is selected. In more detail, when the motor 61i rotates at 6000 rpm, 0.01 second is required to make a round. Therefore, the number of samplings is calculated to be ten when 1 Hz is selected, and calculated to be five when 2 Hz is selected (step S16).

Then, the measurement is repeatedly conducted while rotating the motor 61i until a predetermined number of samplings is reached (step S17).

After calculating high-frequency components from the resulting measured values (step S18), the accommodation function state is displayed in the display section 66 to indicate the measurement results to the operator (step S19). The measurement is thus completed. In the actual measurement, the refractive power is repeatedly measured while moving the target 62a. The details of the measurement method, calculation of high-frequency components, and the details of the accommodation function state display method are basically the same as those of the eye accommodation function state measurement device disclosed in the patent document 3. Therefore, description of these items is omitted.

As described above, the maximum number of samplings is selected corresponding to the measurement time by changing the number of samplings corresponding to the selected high-frequency component value, thereby controlling the measurement operation so that the measurement stability and the measurement time are optimally balanced.

In the second embodiment, the measurement operation is changed by changing the number of measurement samplings. The measurement operation may also be changed by controlling the rotational speed of the motor corresponding to the measurement time.

In the second embodiment, the number of samplings in the normal measurement is set at 20. However, the number of samplings is not limited thereto.

The number of samplings may be set at one, and only the measurement interval from one measurement to the next measurement may be changed.

The high-frequency component input section need not necessarily be provided. The measurement may be conducted at a predetermined high-frequency component value.

The invention claimed is:

1. An eye refractive power measurement device comprising:
   a refractive power measurement section which measures refractive power of a subject's eye;
   a measurement type select section which selects between at least two types of measurements including normal refractive power measurement, which measures the refractive power of the subject's eye including spherical power, cylinder power, and astigmatism axis, and eye accommodation function state measurement, which continuously determines a sequential change in the refractive power of the subject's eye for high-frequency components of 1 Hz to 2.3 Hz at high speed; and
   a control section which changes a measurement operation corresponding to the measurement type selected by the measurement type select section.

2. The eye refractive power measurement device according to claim 1, wherein the measurement operation is changed by changing a number of measurement meridian directions.

3. The eye refractive power measurement device according to claim 1, wherein the measurement operation is changed by changing a number of measurement samplings for obtaining one measured value.

4. The eye refractive power measurement device according to claim 1, wherein the measurement operation is changed by changing a measurement interval from one measurement to next measurement.

5. The eye refractive power measurement device according to claim 1, comprising:
   a motor for projecting a measurement striped pattern onto the subject's eye and moving the striped pattern relative to the subject's eye;
   wherein the measurement operation is changed by changing a rotational speed of the motor.

* * * * *